United States Patent
Majeed et al.

(10) Patent No.: US 6,849,645 B2
(45) Date of Patent: Feb. 1, 2005

(54) METHOD OF INCREASED BIOAVAILABILITY OF NUTRIENTS AND PHARMACEUTICAL PREPARATIONS WITH TETRAHYDROPIPERINE AND ITS ANALOGUES AND DERIVATIVES

(75) Inventors: Muhammed Majeed, Piscataway, NJ (US); Vladimir Badmaev, Piscataway, NJ (US); Rajinder Kumar Bammi, Bangalore (IN); Subbalakshmi Prakash, Piscataway, NJ (US); Sankaran Natarajan, Bangalore (IN)

(73) Assignees: Sabinsa Corporation, Piscataway, NJ (US); Sami Labs LTD, Bangalore (IN)

( * ) Notice: Subject to any disclaimer, the term of this patent is extended or adjusted under 35 U.S.C. 154(b) by 0 days.

(21) Appl. No.: 09/860,816

(22) Filed: May 21, 2001

(65) Prior Publication Data

US 2002/0058695 A1 May 16, 2002

Related U.S. Application Data

(60) Provisional application No. 60/205,245, filed on May 19, 2000, and provisional application No. 60/277,979, filed on Mar. 23, 2001.

(51) Int. Cl.$^7$ ............... A61K 31/445; A61K 31/36
(52) U.S. Cl. ........................ 514/321; 514/464
(58) Field of Search .................. 514/321, 464

(56) References Cited

U.S. PATENT DOCUMENTS

| | | | | |
|---|---|---|---|---|
| 5,744,161 A | * | 4/1998 | Majeed et al. | .............. 426/651 |
| 6,346,539 B1 | * | 2/2002 | Raman et al. | .............. 514/321 |

OTHER PUBLICATIONS

"Synergists for Pyrethrum: Synthetic Analogues of Some Piper Compounds" Atal et al. Indian J. Exp. Biol., vol. 15 Dec. 1977.*

* cited by examiner

Primary Examiner—Sreeni Padmanabhan
Assistant Examiner—Jennifer Kim
(74) Attorney, Agent, or Firm—Arent Fox PLLC

(57) ABSTRACT

Tetrahydropiperine and analogs and derivatives thereof, including dihydropiperine, are disclosed to enhance the absorption and/or bioavailablity of nutrients, drugs and other organic compounds, such as insectides.

21 Claims, 1 Drawing Sheet

OVERLAIN SPECTRA OF BMDP AND PE
(UV / VISIBLE SPECTROPHOTOMETER DATA)

METHOD OF INCREASED BIOAVAILABILITY OF NUTRIENTS AND PHARMACEUTICAL PREPARATIONS WITH TETRAHYDROPIPERINE AND ITS ANALOGUES AND DERIVATIVES

This application claims the benefit of U.S. Provisional Application Nos. 60/205,245 filed May 19, 2000 and 60/277,979, filed Mar. 23, 2001.

FIELD OF THE INVENTION

The present invention is related to the effects of tetrahydropiperine and its analogs or derivatives, such as alkyltetrahydropiperines, e.g. methyltetrahydropiperine, dialkyltetrahydropiperines, e.g. dimethyltetrahydropiperine, alkoxylated tetrahydropiperine, 1-[(5,3-benzodioxyl-5-yl)-1-hydroxy-2,4-pentadienyl]-piperine, 1-[(5,3-benzodioxyl-5-yl)-1-methoxy-2,4-pentadienyl]-piperine, 1-[(5,3-benzodioxyl-5-yl)-1-oxo-4-halo-2-pentenyl]-piperine, 1-[(5,3-benzodioxyl-5-yl)-1-oxo-2-halo-4-pentenyl]-piperine, dihydropiperine, alkyldihydropiperines, dialkyldihydropiperines, and alkoxylated dihydropiperine, on the bioavailability and/or absorption of nutrients and/or drugs in humans and animals.

BACKGROUND OF THE INVENTION

Piperine, an alkaloid naturally occuring in plants from family *Piperacea*, was found to enhance the absorption and/or bioavailability of nutrients[1-3] and drugs.[4-7] In a related prior art reference (Atal, C. K. et al. Indian J Exp Biol; 15 (December 1977): 1230–1232), synthetic derivatives of piperine were shown to exhibit synergism in larvacidal (killing larvae of houseflies) activity when combined with pyrethrin. Pyrethrin is a plant derived compound used as a bug-repellant. The various compounds tested by Atal, C. K. et al. were piperidine amides of tetrahydropiperic acid. Totally, 24 amides and 7 esters of tetrahydropiperic acid were prepared. *Curcuma longa* (Linn. Vern.: turmeric), *Boswellia serrata* (Roxb. Vern.: frankincense) and closely related *Commiphora mukul* (Hook, Vern.: gum-guggul) have been traditionally used in traditional Indo-Tibetan medicine as NSAIDs and in anti-neoplastic therapy.

Curcumin, demethoxycurcumin and bisdemethoxycurcumin (diferuloylmethane derivatives also referred to as curcuminoids), the naturally occurring yellow pigments in turmeric, inhibit gastrointestinal tumorigenesis during initiation and promotion in the experimental models. Possible mechanism may involve inhibition of nitric oxide synthase (iNOS), cyclooxygenase-2 (COX-2) and production of proinflammatory prostaglandins. Topical application of curcuminoids inhibits benzo[a]pyrene (B[a]P)-mediated formation of DNA-B[a]P adducts in the epidermis. It also reduces 12-O-tetradecanoylphorbol-13-acetate (TPA)-induced increases in skin inflammation, epidermal DNA synthesis, ornithine decarboxylase (ODC) mRNA level, ODC activity, hyperplasia, formation of c-Fos, and c-Jun proteins, hydrogen peroxide, and the oxidized DNA base 5-hydroxymethyl-2'-deoxyuridine (HmdU).

Four major triterpene boswellic acids derived from frankincense gum inhibited in vitro the synthesis of DNA, RNA and protein in human leukemia HL-60 cells in a dose dependent manner with IC50 values ranging from 0.6 to 7.1 microM.(see U.S. Ser. No. 09/302,510 filed Apr. 30, 1999, the disclosure of which is hereby incorporated by reference).

The ferulate derivatives isolated from gum guggl showed a significant cytotoxic activity towards MCF-7 (breast) and PC-3 (prostate) tumor cells. The $IC_{50}$ in both cells were 14.3 mcg/ml (25 $\mu$m). The ferulate derivatives decreased cell viability with $IC_{50}$<25 $\mu$m in both transfected (P388/MDR) and parental cell lines. This finding suggests that these compounds might be able to overcome P-glycoprotein mediated drug resistance. (see U.S. Ser. No. 60/205,466 filed May 19, 2000, the disclosure of which is hereby incorporated by reference).

The above mentioned anti-cancer therapies have limitations in efficacy due to poor gastrointestinal absorption and/or insufficient tissue bioavailability of the compounds. The invention relates to of a compound developed from a natural alkaloid, piperine. The natural alkaloid, piperine, has been previously evaluated in oral dosages for its potential to enhance the gastrointestinal absorption of drugs and nutrients in animals and humans. Compounds successfully studied include drugs such as vasicine, pyrazinamide, rifampicin, isoniazid, propranolol, theophylline and phenytoin, and nutrients such as fat soluble beta-carotene, water soluble vitamin B6, vitamin C, coenzyme Q10 and the mineral selenium in the form of L-selenomethionine.

SUMMARY OF THE INVENTION

The present invention concerns a modified alkaloid piperine, in the form of tetrahydropiperine or THP, and analogs and derivatives thereof, which previously have not been studied for its nutrient/drug bioavailability enhancing properties. Based on initial research, the present invention has the property of enhancing the absorption of curcuminoids and other poorly absorbable anticancer drugs through the skin and gastrointestinal tract.

The present invention pertains to tetrahydropiperine and its analogs or derivatives, such as alkyltetrahydropiperines, e.g. methyltetrahydropiperine or ethyltetrahydropiperine, dialkyltetrahydropiperines, e.g. dimethyltetrahydropiperine or diethyltetrahydropiperine, alkoxylated tetrahydropiperine, e.g. methoxy tetrahydropiperine, hydroxylated tetrahydropiperine, e.g. 1-[(5,3-benzodioxyl-5-yl)-1-hydroxy-2,4-pentadienyl]-piperine, 1-[(5,3-benzodioxyl-5-yl)-1-methoxy-2,4-pentadienyl]-piperine, halogenated tetrahydropiperine, e.g. 1-[(5,3-benzodioxyl-5-yl)-1-oxo-4-halo-2-pentenyl]-piperine and 1-[(5,3-benzodioxyl-5-yl)-1-oxo-2-halo-4-pentenyl]-piperine, dihydropiperine, alkyldihydropiperines, e.g. methyldihydropiperine or ethyldihydropiperine, dialkyldihydropiperines, e.g. dimethyldihydropiperine or diethyldihydropiperine, alkoxylated dihydropiperine, e.g. methoxy dihydropiperine, and halogenated dihydropiperine, as enhancers of nutrient or drug bioavailability and of the absorption of nutrients and/or drugs. The present invention also provides compositions containing nutrients and/or drugs, together with tetrahydropiperine or its analogs or derivatives.

DETAIL DESCRIPTION OF THE INVENTION

Figure 1:
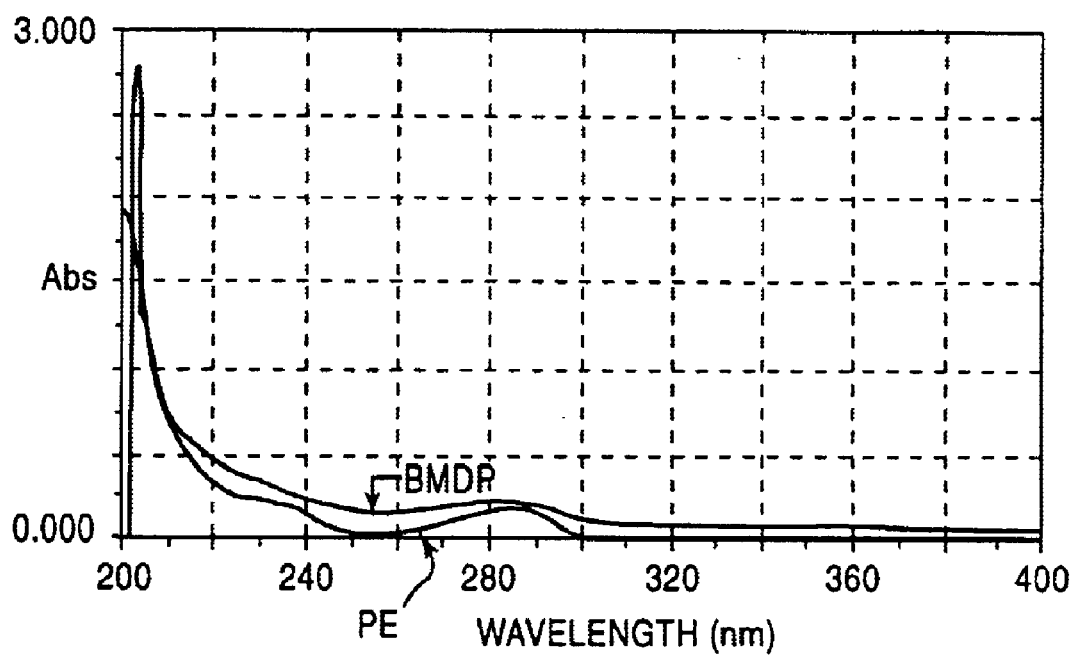
FIG. 1 shows the UV and visible spectra of betamethasone diproprionate and tetrahydropiperine superimposed.

Tetrahydropiperine, the subject of this invention, occurs like piperine natrally in black pepper (about 0.7% in black pepper oleoresin). In the present invention, Tetrahydropiperine was synthesized from piperine which was previously extracted from black pepper oleoresin. The invention was studied in several applications to increase the absorption and/or bioavailability in biological systems. The cited experiments exemplify part of a much broader application of invention for nutrient/drug absorption and/or bioavailability. The present inventors demonstrate, for the first time, that certain synthetic derivatives of piperine, such as tetrahydropiperine and its analogs or derivatives, affect the bioavailability and/or absorption of nutrients and/or drugs.

Within the scope of the present invention is a method of increasing nutrient or drug bioavailability in an animal or human subject in need of such an increase, comprising administering a nutrient or drug bioavailability increasing effective amount of tetrahydropiperine, or an analog or derivative thereof, such as alkyltetrahydropiperine, e.g. methyltetrahydropiperine, ethyltetrahydropiperine, propyltetrahydropiperine, dialkyltetrahydropiperine, e.g. dimethyltetrahydropiperine or diethyltetrahydropiperine, alkoxylated tetrahydropiperine, e.g. methoxy tetrahydropiperine or ethoxy tetrahydropiperine, 1-[(5,3-benzodioxyl-5-yl)-1-hydroxy-2,4-pentadienyl]-piperine, 1-[(5,3-benzodioxyl-5-yl)-1-methoxy-2,4-pentadienyl]-piperine, halogenated tetrahydropiperine, e.g. 1-[(5,3-benzodioxyl-5-yl)-1-oxo-4-halo-2-pentenyl]-piperine and 1-[(5,3-benzodioxyl-5-yl)-1-oxo-2-halo-4-pentenyl]-piperine, dihydropiperine, alkyldihydropiperine, e.g. methyldihydropiperine, ethyldihydropiperine or propyldihydropiperine, dialkyldihydropiperine, e.g. dimethyldihydropiperine or diethyldihydropiperine, alkoxylated dihydropiperine, e.g. methoxy dihydropiperine or ethoxy dihydropiperine, or halogenated dihydropiperine, e.g. 1-[(5,3-benzodioxyl-5-yl)-1-oxo-2-chloro-4-pentenyl]-piperine and 1-[(5,3-benzodioxyl-5-yl)-1-oxo-4-chloro-2-pentenyl]-piperine, to the subject, at or near the time the subject takes the drug or nutrient.

Also within the scope of the present invention is a method of increasing absorption of a nutrient and/or drug in an animal or human subject in need of such an increase, comprising administering a absorption increasing effective amount of tetrahydropiperine, or an analog or derivative thereof, such as alkyltetrahydropiperine, e.g. methyltetrahydropiperine, ethyltetrahydropiperine, propyltetrahydropiperine, dialkyltetrahydropiperine, e.g. dimethyltetrahydropiperine or diethyltetrahydropiperine, alkoxylated tetrahydropiperine, e.g. methoxy tetrahydropiperine or ethoxy tetrahydropiperine, hydroxylated tetrahydropiperine, 1-[(5,3-benzodioxyl-5-yl)-1-hydroxy-2,4-pentadienyl]-piperine, halogenated tetrahydropiperine, e.g. 1-[(5,3-benzodioxyl-5-yl)-1-methoxy-2,4-pentadienyl]-piperine and 1-[(5,3-benzodioxyl-5-yl)-1-oxo-4-halo-2-pentenyl]-piperine, 1-[(5,3-benzodioxyl-5-yl)-1-oxo-2-halo-4-pentenyl]-piperine, dihydropiperine, alkyldihydropiperine, e.g. methyldihydropiperine, ethyldihydropiperine or propyldihydropiperine, dialkyldihydropiperine, e.g. dimethyldihydropiperine or diethyldihydropiperine, alkoxylated dihydropiperine, e.g. methoxy dihydropiperine or ethoxy dihydropiperine, hydroxylated dihydropiperine, or halogenated dihydropiperine, e.g. 1-[(5,3-benzodioxyl-5-yl)-1-oxo-2-chloro-4-pentenyl]-piperine or 1-[(5,3-benzodioxyl-5-yl)-1-oxo-4-chloro-2-pentenyl]-piperine, to the subject, at or near the time the subject takes the drug or nutrient.

In this patent application, the term "nutrients" includes amino acids (both nonessential amino acids and essential amino acids, such as leucine, isoleucine, valine, phenylalanine, tryptophan, histidine, threonine, methionine and lysine), carbohydrates (such as glucose, fructose and lactose), vitamins (both water-soluble vitamins, such as vitamin B1, vitamin B2, niacinamide, vitamin B6, vitamin B12, folic acid, and vitamin C, and fat-soluble vitamins, such as vitamin A, vitamin D, vitamin E and vitamin K), minerals (such as calcium, magnesium, zinc, copper, selenium, iron, vanadium, chromium, iodine, potassium, and manganese), herbal extracts (such as curcumin, curcuminoids, boswellic acids, ashwagandha, *Ginkgo biloba,* capsaicin, aconitine and St. John's wort), and antioxidants (such as vitamin A, vitamin C, vitamin E, alpha-carotene, transbeta-carotene, betacryptoxanthin, lycopene, lutein/zeaxanthin, pine bark bioflavonals complex, germanium, selenium and zinc).

In this patent application, the term "drugs" include anti-tumor agents (such as methotrexate, mercaptopurine, fluorouracil, floxuridine, lomustine, busulfan, cisplatin, bleomycin, doxorubicin, daunorubicin, vincristine, vinblastine, paclitaxel, and tamoxifen), anti-viral agents (such as amantadine, rimantadine, ribavirin and anti-HIV agents, e.g zidovudine, didanosine, dideoxycytosine, didoxyinosine, stavudine, lamivudine, and protease inhibitors), antibacterial agents (such as penicillins and cephalosporins), antifungal agents (such as amphotericin B), anti-parkinsonism agents (such as L-DOPA), antiepileptics, analgesics (such as opioid analgesics, e.g. morphine, methadone, codeine, hydrocodone, and meperidine, and non-steroidal anti-inflammatory analgesics, e.g. diclofenac diethyl ammonium), anti-arrhythmic agents (such as quinodine, lidocaine, flecainide, beta-adrenergic blockers, e.g. propranolol and sotalol, amiodarone, calcium channel blockers, e.g. verapamil and diltiazem), anti-anginal agents (e.g. amiodipine, bepridil, nifedipine, and dipyridamole), anti-hyperlipidemic agents (e.g. gemfibrozil, probucol, lovastatin, simvastatin, and pravastatin), anti-hypertensive agents (e.g. diuretics, e.g. thiazide diuretics, furosemide, torsemide, triamterene, amiloride, clonidine, beta-adrenergic blockers, e.g. acebutolol, atenolol, betaxolol, bisoprolol, and metoprolol, alpha-adrenergic blockers, e.g. prazosin and terazosin, hydralazine, minoxidil, angiotensin converting enzyme inhibitors, e.g. captopril, benzazepril, and enalapril, diazoxide, and nitroglycerin), corticosteroids (such as betamethasone, dexamethasone, flunisolide and triamcinolone), cromolyn sodium, nedocromil, albuterol, and bitolterol.

In the present patent application, the term "alkyl" includes a $C_1$–$C_6$, preferably $C_1$–$C_3$, and more preferably $C_1$, straight or branched aliphatic, optionally substituted, hydrocarbyl group. The optional substituents can be halo, hydroxy, $C_1$–$C_6$ alkoxy, sulfydryl, amino and/or nitro groups.

The term "halo" means fluoro, chloro, bromo, or iodo. Preferably, "halo" is chloro or bromo.

The term "absorption" includes the absorption via a parenteral, gastrointestinal (such as after oral administration), sublingual, topical (such as via dermal route, opthalmic route, or via the administration of suppositories), and/or inhalation administration. The term "bioavailability" means the amount of the nutrient or drug available in the body of the subject who takes the nutrient or drug by the parenteral administration, gastrointestinal, sublingual, topical (such as via dermal route, opthalmic route, or via suppositories), and/or inhalation route.

The present invention also includes compositions or formulations comprising tetrahydropiperine, an analog or derivative of tetrahydropiperine, such as alkylated tetrahydropiperine or dihydropiperine, or pharmaceutically acceptable salts of tetrahydropiperine or an analog or derivative of tetrahydropiperine, in admixture with a pharmaceutically acceptable carrier or excipient. Optionally, the compositions or formulations may further comprise a nutrient or drug.

Another aspect of the present invention is tetrahydropiperine, the analogs of tetrahydropiperine, the derivatives of tetrahydropiperine, and the pharmaceutically acceptable salts of tetrahydropiperine and the analogs and the derivatives of tetrahydropiperine. The "analogs" of tetrahydropiperine are chemical compounds having a structure similar to tetrahydropiperine, so that the "analogs" have similar biological effects as tetrahydropiperine in increasing the bioavailability of nutrients and/or drugs and/or in increasing the absorption of nutrients and/or drugs. The "derivatives" of tetrahydropiperine are chemical compounds derived from tetrahydropiperine, e.g. by the addition of a substituent or functional group or by the removal of a functional group. Examples of the analogs and derivatives of tetrahydropiperine are disclosed above.

Tetrahydropiperine and analogs or derivatives of tetrahydropiperine, e.g. dihydropiperine, can be administered to an animal or human subject in need of an increase in bioavailability or absorption of a nutrient and/or a drug in the methods of the present invention at a dose of about 0.00005 to 50 mg/kg body weight of the subject per day, about 0.00005 to 0.99 mg/kg body weight per day, or 1 to 50 mg/kg body weight per day. Preferably, the dose is 0.00005 to 0.5 mg/kg per day. More preferably, the dose is 0.00005 to 0.15 mg/kg per day. Even more preferably, the dose is 0.0005 to 0.015 mg/kg per day.

Tetrahydropiperine and dihydropiperine can be prepared by reduction of piperine with a reductive procedure known in the art. For instance, tetrahydropiperine is prepared by reduction of piperine with hydrogenation using Pd/C as a catalyst. Dihydropiperine can be produced by hydrogenation of piperine catalyzed by chlorotris(triphenylphosphine) rhodium or hydrogenation of piperine using Pd/C as a catalyst at a temperature or pressure lower than the preparation of tetrahydropiperine from piperine. The preparation of derivatives or analogs of tetrahydropiperine can be performed using synthetic procedures known in the art. For instance, conversion of the oxo group of tetrahydropiperine or dihydropiperine to a hydroxy group can be performed by reduction of the carbonyl group with hydrogen and a Rh catalyst or $Bu_3SnH$—$Pd(PPh_3)_4$. Halo derivatives of tetrahydropiperine or dihydropiperine can be prepared by addition of HF, HCl, HBr or HI to the C=C bond of the compound. The starting material, piperine, can be prepared via synthetic methods or via extraction of black pepper or Piper longum by methods known in the art.

In another aspect of the present invention, a study was conducted to determine whether a topical composition containing THP (98% purity), at a level of 0.01% and 0.1% by weight, which is preferred topical dose range for the compound, would produce symptoms of topical irritation. A skin patch test using THP in a petrolatum vehicle was conducted on 50 healthy volunteers for 48 hr with reading of the results after 48 hr and 72 hr. Neither dose caused skin irritation at the time of clinical evaluation of the study subjects. The irritation score was reported by the supervising physician, a practicing dermatologist, as 0. These results indicate that THP does not act as a skin irritant at a dose range considered effective for topical delivery. Based on previous experience with the parent compound, THP should not irritate the stomach mucosa at dose level of up to 50 mg per os in an adult healthy volunteer.

The drug enhancing potential of THP was evaluated in experiments with two poorly absorbable drugs, the steroidal anti-inflammatory drug Betamethasone dipropionate, or BMDP, and the antioxidant phenolic compounds tetrahydrocurcuminoids (THC).

In the experiment involving BMDP, the skin preparation was mounted in a Franz Diffusion Cell which resulted in two compartments; "donor" and "receptor". The drug (100 ug/ml) was applied with 0.1% (active sample) or without (control sample) of THP in the donor compartment. Subsequently the absorbencies of the fluid in the receptor compartment for the presence of BMDP and THP were measured in time intervals of 5, 10, 15, 20, 30, 45 and 60 minutes. The active sample resulted in 100% diffusion of the BMDP within the first 10 minutes. The control sample resulted in 29% diffusion of BMDP after 45 minutes and only 54% diffusion after 60 minutes.

The bioenhancing potential of THP on the free-radical scavenging properties of topically applied THC was evaluated. In this in vitro DPPH radical scavenging method, the ability of an anti-oxidant to bind and inactivate the 1,1 diphenyl-2-picrylhydrazyl radical, or DPPH, was measured. DPPH is considered an example of a very stable free radical. The control sample contained 0.01% of THC while active samples contained 0.01% of THC with THP concentrations ranging from 0.1%–0.0001%. Additionally, controls containing various concentrations of THP alone were also tested for DPPH binding.

While THP by itself did not show any significant antioxidant properties, together with THC it was shown to enhance the antioxidant properties of THC by up to 30% as compared to when THC was used alone. Even in its highest dilution of 0.0001% THP still displayed some beneficial THC bioenhancing activity.

The invention therefore enhances topical and systemic absorption of curcuminoids and their THC derivatives which in turn promotes the known anticancer properties of curcuminoids. A preferred method of the invention is used to treat prostate cancer due to the systemic increase of phenolic compounds.

Further, THP may theoretically exert the anticancer effects on its own since its parent compound piperine is known to flush the neurotransmitters, such as substance P, from the nerve endings. Preventing neurotransmitters from the site of the cancer, as discussed above, could prevent stimulation of the androgen receptor and ultimately the growth of cancer cells.

The composition of the present invention may be administered to a patient, preferably a human, by parenteral administration, or, more preferably, orally or topically.

The amount of THP in a drug composition in a unit dose suitable for oral administration generally ranges from 0.0004–0.85 mg/kg of body weight; for parenteral administration in a unit dose from 0.00004–0.085 mg/kg of body weight; and for topical administration the amount of THP will range from 0.00001%–10%, preferably 0.001% to 5% by weight, based on the total weight of the topical composition.

Thus, one aspect of the present invention relates to the use of tetrahydropiperine in compositions to be administered together with anticancer drugs. The compounds administered in conjunction with tetrahydropiperine can include curcuminoids, boswellic acids, and other botanical or synthetic compounds having biological activities against prostate cancer and poor absorbability. The amount of the anticancer compounds to be administered to a patient will vary, depending upon the known anticancer effective amounts of these active compounds, although frequently the enhancement of the absorption of these compounds permits lesser amounts of the compounds to be administered while retaining the anticancer effect.

Normally the weight ratio of THP: poorly absorbable anticancer compound or other drug will range from 1:01–10, although it is believed that amounts outside of this range will be effective for at least some of the anticancer compounds or other drugs contemplated for use in the present invention.

The present invention is illustrated with working examples below, which is for illustration purpose only and should not be construed to limit the scope of the invention.

EXAMPLE 1

The effect of tetrahydropiperine was evaluated on the dermal absorption of a steroidal anti-inflammatory drug, Betamethasone dipropionate (BMDP).

Materials and Methods:

Franz diffusion cell was utilized in the experiment. This is an in vitro set-up prepared from the graft of the abdominal skin of mouse to evaluate absorption of drugs and nutrients through the skin. The Franz diffusion cell contains Donor and Receptor compartments. The test drug, BMDP, with or without tetrahydropiperine (Control) was applied on one side of the skin (Donor compartment). The drug's transport to the Receptor side of the skin was estimated by UV method at pre-determined time intervals.

Instruments:

Franz diffusion cell (Fabricated); Capacity of receptor compartment-36 ml; Area of skin mounted-10.18 sq.cm; UV/VIS Spectrophotometer (JascoV-530), FT/IR Spectrophotometer (Jasco 5300).

Chemicals

Betamethasone dipropionate (Nucron Pharmaceuticals Ltd.); Sodium chloride; Tween 20; Propylene glycol; All chemicals were of analytical grade.

1. Standard BMDP Solution (100 µg/ml):
   In a volumetric flask of 100 ml, 10 mg of BMDP was taken and dissolved in 50 ml Saline with Tween solution and volume was made up with the same.
2. Tetrahydropiperine Solution (1% w/v):
   In a volumetric flask of 25 ml, 0.25 g of tetrahydropiperine was made up with Propylene glycol (PG).

Preparation of Skin:

The abdominal skin of albino mice of either sex was used. The mice used were of age 7–8 weeks. The mice were sacrificed by tail plucking method. The abdominal skin of mice was shaved, excised and adhering fatty tissues were removed. Skin was stored in saline solution (0.9% w/v) for hydration upto one hour.

Experimental Design:

The hydrated skin was mounted on Franz diffusion cell with shaved surface facing the donor compartment. The receptor fluid (Saline with Tween 20 Solution) was, maintained at 37±0.5° C. and stirred continuously at 200 rpm. The experiments conducted are described below:

a. Control: 0.5 ml of Propylene glycol was applied to mounted skin and kept for one hour. Receptor fluid was removed and replaced with fresh receptor fluid. 0.5 ml of BMDP solution (50 µg) was applied and sampling was carried out for a period of 3 hrs. The sample volume was 2 ml each time, which was replaced by fresh receptor fluid. Absorbance of each sample was measured by UV spectrophotometer at the wavelength of 256 nm.

b. Test: 0.5 ml of tetrahydropiperine solution was applied to mounted skin and kept for one hour. The receptor fluid was removed and replaced with fresh receptor fluid. 0.5 ml of BMDP solution (50 µg) was applied and sampling was carried out for a period of 3 hrs. The sample volume was 2 ml each time, which was replaced by fresh receptor fluid. Absorbance of each sample was measured by UV spectrophotometer at the wavelength of 256 nm.

UV absorption Spectra of BMDP solutions show absorption at 238 nm when prepared in saline with tween 20 solution. We selected 256 nm as a wavelength of analysis for the following reasons.

1. Tetrahydropiperine gave absorbance at 228 nm and 275 nm.
2. The absorbance of tetrahydropiperine was minimum at 256 nm while it was good for BMDP. The difference in the absorption value at $\lambda 256$ is the maximum.
3. Calibration curve was prepared using receptor fluid to simulate the conditions for BMDP, present in test solution.

TABLE 1

Calibration curve for Betamethasone Dipropionate in saline with tween 20 (0.05%); $\lambda 256$ nm.

| Conc. (µg/ml) | Absorbance |
|---|---|
| 5 | 0.090 |
| 10 | 0.12 |
| 15 | 0.147 |
| 20 | 0.197 |
| 25 | 0.248 |
| 30 | 0.310 |

Considering that absorbance is an additive property, concentration of BMDP in the permeation study was determined by exploiting the curve subtraction facility of software V500 provided by Jasco. The absorbance at 256 nm of the spectrum was obtained by subtracting the curve spectrum of tetrahydropiperine from the spectrum of BMDP with tetrahydropiperine. The percentage of drug diffused in control and test are given in Table 2.

TABLE 2

Effect of tetrahydropiperine on transdermal diffusion of BMDP.

| Time (Min) | Percent Diffuse | |
|---|---|---|
| | Control | Test |
| 5 | — | 95.06 |
| 10 | — | 102.55 |
| 15 | — | — |
| 20 | — | — |
| 30 | — | — |
| 45 | 29.05 | — |
| 60 | 53.847 | — |

From the above table it is observed that in first 30 mins the amount of drug diffused in control is undetectable. However, in presence of tetrahydropiperine all the drug has diffused within 10 min. This demonstrates the increased permeation of BMDP in the presence of Tetrahydropiperine.

EXAMPLE 2

In vitro permeation studies of Forskholin, a diterpenoid compound which has various therapeutic effects (Bronchodilation—used in Asthma, prevents platelet aggregation, anti hypertensive, anti glaucoma and anti-inflammatory) was carried out. Fabricated Franz diffusion cells of capacity 67 and 69 ml were used for the study. Freshly excised rat abdominal skin was used for the permeation studies.

Apparatus

Fabricated Franz Diffusion Cells

Capacity of the receptor compartment: 67 and 69 ml

Materials and Methods

Solutions Used in the Study a) 2.5% Forskolin in methanol.
b) 0.05% Tetrahydropiperine in 2.5% Forskolin in methanol.
c) 0.1% Tetrahydropiperine in 2.5% Forskolin in methanol.

Procedure

Freshly excised rat abdominal cell was mounted on the Franz diffusion Cell, the outer layer of the skin facing the donor compartment. The receptor fluid was maintained at 35° C. using a thermostatic magnetic stirrer.

The study was conducted by replacing the medium in the receptor compartment with methanol instead of phosphate buffer. In both the receptor and donor compartment methanol was used as the medium in the permeation studies.

Test

In the donor compartment 2 ml methanol containing 50 mg of Forskolin and tetrahydropiperine (5% of Forskolin conc.) was taken. Receptor compartment consisted of 69 ml of methanol maintained at 35° C. Permeation study was carried out for a period of 1 hr. Samples were withdrawn at 15, 30 and 60 minutes intervals and the amount of Forskholin present was analyzed by HPLC.

Control

In the donor compartment 2 ml methanol containing 50 mg of Forskholin was taken. Receptor compartment consisted of 65 ml of methanol maintained at 35° C. Permeation study was carried out for a period of 1 hour. Samples were withdrawn at 15, 30 and 60 minutes intervals and the amount of Forskholin present was analyzed by HPLC.

Results

FIG. 1 shows the transdermal permeation of Forskolin in the presence and absence of tetrahydropiperine (5% of Forskolin conc.) Table 2 gives a comparative release data of Forskholin in the presence and absence of tetrahydropiperine.

TABLE 2

Transdermal Release/Permeation of Forskolin

| Time in min | Forskolin Release Control | Forskolin Release with THP | Increase in release (% of Forskolin) |
| --- | --- | --- | --- |
| 15 | 1.28 | 1.64 | 28.12 |
| 30 | 4.05 | 5.64 | 39.25 |
| 60 | 8.45 | 8.88 | 5.09 |

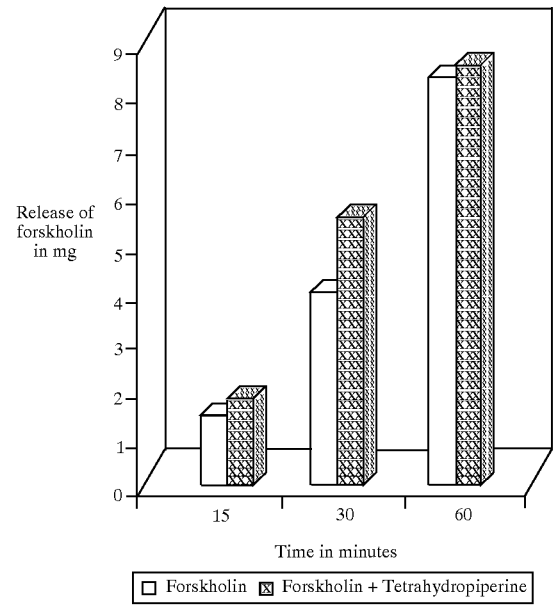

FIG. 1
FORSKOLIN IN THE GRAPH

In vitro transdermal permeation of forskholin in the presence of tetrahydropiperine Conclusion: The permeation of Forskolin was enhanced when the concentration of Tetrahydropiperine was 5% of Forskolin concentration. However, when the concentration of tetrahydropiperine was 2% of Forskolin concentration, enhanced permeation was not observed.

EXAMPLE 3

The tetrahydropiperine was tested against tobacco cut worm, Spodoptera litura F. to determine its possible increased kill rate when used with Fenvalerate—a synthetic pyrethroid.

The experiment demonstrates the ability of Tetrahydropiperine to enhance the penetration of Fenvalerate. Because of this enhanced penetration the kill rate is significantly higher compared to that of control. Details of this example are given in the following paragraphs:

Methodology a. Preparation of test solution—0.5 g of the test product was dissolved in 1 ml of Ethanol and made up to 100 ml in standard volumetric flask using suitable emulsifier. This solution contains 5000 ppm a.i. (0.5 percent). Further, serial dilution was made to get 0.25, 0.125 and 0.0625% of the test product. To each of these test solutions, Fenvalerate was added to get 250 ppm of Fenvalerate a.i. in the final volume. For comparison 0.5 percent of Tetrahydropiperine, Ethanol 1.0 percent solution and 250 ppm a.i. of Fenvalerate was used.

b. Bioassay—Laboratory reared 7 day old larvae of tobacco cut worm, Spodoptera litura were used in the experiment. After a series of preliminary tests the concentrations chosen for the experiment were 0.5, 0.25, 0.125 and 0.0625 percent tetrahydropiperine. Fresh castor leaves were dipped for 30 seconds in above concentrations of test and standard compounds and blank solutions. After proper drying, the treated leaves were transferred to plastic containers. To each container 5 larvae were released. This was repeated four times so as to have 20 larvae for each concentration. Larvae in control set were fed with leaves dipped in water. Observations were recorded for larval mortality after 48 hours of exposure.

Results

From the results tabulated in Table 1

| TREATMENT | CONCENTRATIONS | PERCENT MORTALITY* (Mean of 4 replications) |
|---|---|---|
| 1. Tetrahydropiperine | a) 0.0625% + 250 ppm a.i. Fenvalerate | 50 |
| | b) 0.125% + 250 ppm a.i. Fenvalerate | 65 |
| | c) 0.25% + 250 ppm a.i. Fenvalerate | 85 |
| | d) 0.5% + 250 ppm a.i. Fenvalerate | 100 |
| 2. Tetrahydropiperine | 0.5% | 0 |
| 3. Fenvalerate | 250 ppm a.i. | 55 |
| 4. Ethanol (99%) | 1% | 0 |
| 5. Control | — | 0 |

*Recorded at 48 hours. Mean of 4 replications a.i.—Active Ingredient

It is observed that the mortality is dependent on the dose of the test compound tetrahydropiperine. At 0.0625%, the test compound did not enhance the activity of 250 ppm a.i. of Fenvalerate. At 0.125% there was slight increase in activity resulting in 65 percent kill of the test insect. At concentration levels 0.25 and 0.5 percent with 250 ppm. a.i. of Fenvalerate the mortality obtained was 85 and 100 percent respectively, as against 55 percent in standard alone treatment of 250 ppm a.i. of Fenvalerate. The test compound tetrahydropiperine by itself at its highest dilution of 0.5% did not show any activity on the target insect.

Conclusion

The tobacco cut worm; *Spodoptera litura* is becoming a hazard on a variety of crops. Many insecticides being targeted against this pest, which is resistant to some of these insecticides. Though the mechanisms of resistance could be many, the difficulty in cuticular penetration could be one of the factors responsible for imparting the physiological resistance.

The Fenvalerate was more effective because of its improved cuticular penetration, brought about by Tetrahydropiperine).

The "synergistic effect" of tetrahydropiperine with pyrethrin as reported by Atal et. al.[8] can now be explained on the basis of the enhanced penetration of pyrethrin in bodies of larvae of houseflies because of increased skin permeability due to tetrahydropiperine as demonstrated in this application.

EXAMPLE 4

An experiment to see how tetrahydropiperine enhances the skin permeability of anthelmintic drugs such as albendazole on intestinal worms was conducted. However, as a preliminary study towards this, tests on earthworms were conducted.

Materials and Methods:

Earthworms were obtained from the Al Ameen College of Pharmacy, Bangalore. Albendazole (Zentel) was obtained from Smith Kline Beecham Pharmaceuticals, Bangalore. The aqueous test solution contained tetrahydropiperine (Tetraperine™, A proprietary product of Sabinsa Corporation, USA) of 0.1% and 0.2% w/v suspended in 0.25% w/v sodium carboxy methyl cellulose.

Experimental Procedure:

1. Effect of Albendazole: Earth worms of similar length and weight were divided into three groups of six worms each. The worms were exposed to tetrahydropiperine 0.1% and 0.2% along with or without Albendazole 0.2%, in a petri dish. The time of onset of paralysis was noted and the death of the worms were observed and recorded as above. The results are presented in table 1 and FIG. 1.

Results & Discussion:

It was found that albendazole 0.1% exerted anthelmintic activity only after 2 hr. Hence, higher concentration of albendazole was used.

At albendazole 0.2% the anthelmintic activity was observed to be within 2 hr. Hence this concentration was selected as standard. With Tetrahydropiperine 0.1% with albendazole 0.2%, no change on the time of paralysis and death was observed, when compared with standard concentration, using unpaired 't' test.

Albendazole 0.2% when co-administered with tetrahydropiperine 0.2% showed a reduction in the time taken for paralysis and death. Hence as the concentration of THP was increased the skin permeability of anthelmintic agents were enhanced.

TABLE 1

Effect of Tetrahydropiperine on Albendazole induced anthelmintic activity.

| Treatment | Time taken in minutes (Mean ± SEM) | | % Reduction in time for | |
|---|---|---|---|---|
| (% w/v) | Paralysis | Death | Paralysis | Death |
| 1. Placebo | — | — | Nil | Nil |
| 2. THP 0.1% | — | — | Nil | Nil |
| 3. Albendazole 0.2% | 99.0 ± 3.93 | 110.33 ± .4.75 | — | — |
| 4. Albendazole 0.2% + THP 0.1% | 86.31 ± 4.3 | 98.16 ± 5.19 | 12.81 | 11.03 |
| 5. Albendazole 0.2% + THP 0.2% | 62.01 ± 3.33 (p < 0.001) | 74.64 ± 2.98 (p < 0.001) | 37.36 | 32.32 | n = 6 in each group and significance is represented by unpaired 't' test

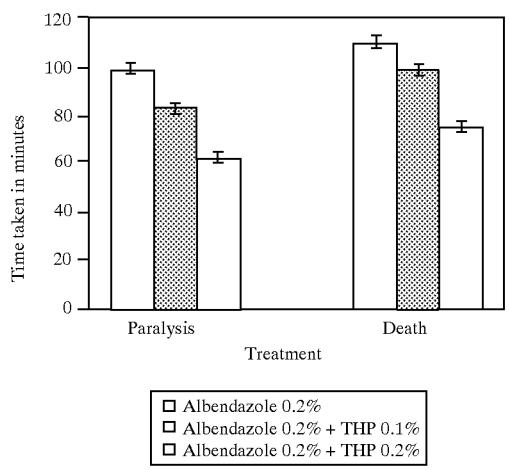

FIG. 1

Effect of Tetrahydropiperine on Albendazole induced anthelmintic activity

Conclusions:

These observations demonstrate that, in presence of Tetrahydrapiperine the anthelmintic activities of albendazole was enhanced. Thus Tetrahydrapiperine could be used as a skin permeability enhancer enabling a lower effective dose of albendazole. The following experimental studies establish the low skin irritation potential of Tetrahydropiperine:

EXAMPLE 5

Determination of Skin Irritation Potential—Animal Studies

The study was designed to determine the primary skin irritation potential on New Zealand White rabbits following the guidelines provided by Gaitonde Committee, CIB, New Delhi, India Test Animals:

New Zealand White, healthy, adult male and female rabbits, each group comprising of 3 randomly selected animals of each sex.

Materials and Methods:

0.5 ml of the test substance was applied to dehaired intact and abraded skin sites of each test animal. Care was taken to note that the abrasions penetrated the Stratum corneum, but not the dermis. A gauze patch was secured over each treated area using tape. The patch and unabsorbed test substance were removed after 24 hours. Each site of application was carefully observed and the reaction evaluated according to Draize's method at 24 and 72 hours.

Results:

No erythema or edema was observed in both intact and abraded skin sites on all the test animals.

Conclusion:

The primary skin irritation score is zero. Tetrahydropiperine did not cause any irritation to the skin in rabbits.

EXAMPLE 6

Determination of Skin Irritation Potential—Patch Test in Humans

The 48 hour Repeat Insult Patch Test was used to evaluate skin irritation potential of the test compound.

Subjects

50 Male or female subjects aged between 18 and 87 years participated in the study. 5 male and 41 female subjects completed the study. The subjects were in good health and using no medications from 30 days prior to the commencement of the study.

Materials and Methods

The test material was applied occlusively, 0.1% w/w diluted in petrolatum. 0.2 g or 0.2 cc of the test material was dispensed into the skin of the upper back. Paper tape such as 3M Micropore™ or Kendall Tenderskin™ was used for fixation after preparation of the surrounding skin with an adhesion enhancer such as Mastitol™. The subject was instructed to avoid exposure to water or to direct sunlight during the 48 hour observation period. The tape was removed at the test facility at the end of the exposure period and evaluated by trained personnel under the supervision of the principal investigator.

Reactions were scored based on the appearance of erythema or edema immediately following removal of the patch and again at 24 hours following removal. Subjects were instructed to report any delayed reactions occurring after the final reading.

Results:

No erythema or edema reactions were observed in any of the subjects after 48 hours exposure of the skin to the test material.

Conclusion:

The test material when tested as described under 48 hour occlusive patch testing on fifty subjects appears not to produce primary (contact) irritation. Therefore Tetrahydropiperine has low skin irritation potential.

EXAMPLE 7

Process of Preparing Tetrahydropiperine

Chemistry of Tetrahydropiperine (THP):

Chemical Name: 1-[5-(1,3-Benzodioxol-5 yl)-1-oxo-pentanoyl]-Piperidine

Molecular formula: $C_{17}H_{23}NO_3$

Molecular weight: 289.36

Percentage composition: C-70.56%, H-8.01%, N-4.84%, O-16.59%

The similarities of the structures of Piperine and THP can be seen and understood by looking at their structures given below:

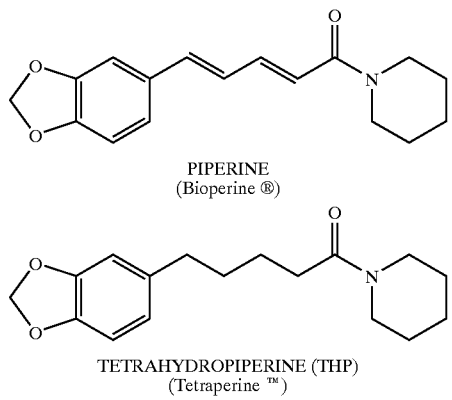

PIPERINE
(Bioperine ®)

TETRAHYDROPIPERINE (THP)
(Tetraperine ™)

Synthesis of Tetrahydropiperine:

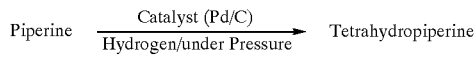

Process:

Piperine was dissolved in a protic solvent such as Methanol, Ethanol, isopropanol etc. The preferred solvent is methanol. A noble metal catalyst such as Pt, $PtO_2$ or Pd on Carbon (5% or 10%) can be used. The preferred one being Pd on Carbon with 5% activity was added as catalyst and hydrogenation was carried out at a pressure ranging from 30 to 80 psi for 2 to 6 hrs. at 25 to 60° C. After completion of reaction, catalyst was filtered off and the filtrate concentrated under vacuum at temperature at 30 to 40° C. The residual oil was cooled to room temperature, seeded with crystals of tetrahydropiperine and left overnight for completion of crystallization. Then it is filtered, dried and stored in a dry place.

Example of the process: 100 gm of piperine was dissolved in 700 ml of methanol. To this mixture 5 gm of 5% Pd/C was added as catalyst and hydrogenation was carried at 40 Psi for two hours at 40 to 50° C. After completion of reaction, catalyst was filtered off and the filtrate concentrated under vacuum at temperature under 40° C. The residual oil was cooled to room temperature, seeded with crystals of tetrahydropiperine and left overnight for completion of reaction.

Specification of THP:

Description: Off-white, low melting solid with characteristic odour.

Solubility: Soluble in chloroform, methanol and insoluble in water.

Melting point: 41° C.–42° C.

Assay by HPLC: min. 99.5%

Chromatographic impurities: Not more than 0.5%

References

1. Majeed et al., (1996) Use of piperine to increase the bioavailability of nutritional compounds. U.S. Pat. No. 5,536,506.
2. Majeed et al., Use of piperine as a bioavailability enhancer.(1998) U.S. Pat. No. 5,744,161.
3. Majeed et al.,(1999) Bioperine applications for nutraceutical bioavailability U.S. Pat. No. 5,972,382.
4. Zutshi, U. et al., (1984). Influence of piperine on rifampicin blood levels inpatients with pulmonary tuberculosis. *J. Assoc. Physicians of India.* 33; 223–224.
5. Zutshi, U. et al. (1989). A process for preparation of pharmaceutical combination with enhanced activity for treatment of tuberculosis and leprosy Indian Patent No. 1232/DEU89.
6. Bano, G. et al. (1991). The effect of piperine on the bioavailability and pharmacokinetics of propranolol and theophylline in healthy volunteers. *European J. Clin. Pharm.* 41; 615–618.
7. Bano, G. et al. (1987). The effect of piperine on the pharmacokinetics of phenytoin in healthy volunteers. *Planta Medica.* 53; 568–570.
8. Atal C. K. et al. (1977). *Indian J. Exp. Biol,* 15; 1230–1232.

What is claimed is:

1. A method of increasing drug bioavailability in a subject in which such increase is desired, comprising administering a bioavailability increasing effective amount of tetrahydropiperine, or an analog or derivative thereof, to said subject, together with or proximate the administration of the drug, wherein the drug is betamethasone dipropionate, diclofenac diethyl ammonium, Forskohlin or an anthelminthic.

2. The method of claim 1, wherein the drug is Betamethasone dipropionate.

3. The method of claim 1, wherein the drug is diclofenac diethyl ammonium.

4. A method for increasing the absorption of a nutrient in a subject in need of such an increase, comprising administering the nutrient and a nutrient absorption increasing effective amount of tetrahydropiperine, or an analog or derivative thereof, to said subject, wherein said subject is a human, wherein the nutrient is selected from the group consisting of amino acids, carbohydrates, vitamins, herbal extracts and antioxidants.

5. The method of claim 4, wherein said absorption is dermal, oral or parenteral absorption.

6. The method of claim 5, wherein said absorption is dermal absorption.

7. The method of claim 1, wherein the subject is a human or animal.

8. The method of claim 1, wherein the drug is Forskohlin.

9. The method of claim 1, wherein the drug is an anthelminthic.

10. The method of claim 1, wherein the analog or derivative is
   alkyltetrahydropiperine, dialkyltetrahydropiperine, alkoxylated tetrahydropiperine, hydroxylated tetrahydropiperine, halogenated tetrahydropiperine, dihydropiperine, alkyldihydropiperine, dialkyldihydropiperine, alkoxylated dihydropiperine, hydroxylated dihydropiperine, or halogenated dihydropiperine, wherein the alkyl groups are independent of 1 to 6 carbon atoms.

11. A method of increasing the bioavailability of a nutrient in a subject in which such increase is desired, comprising administering a bioavailability increasing effective amount of tetrahydropiperine, or an analog or derivative thereof, to said subject, together with or proximate the administration of the nutrient, wherein the nutrient is selected from the group consisting of amino acids, carbohydrates, vitamins, herbal extracts and antioxidants.

12. The method of claim 11, wherein the nutrient is selected from the group consisting of amino acids, carbohydrates, vitamins and herbal extracts.

13. The method of claim 11, wherein the nutrient and the tetrahydropiperine, or an analog or derivative thereof, are administered proximate in time to each other.

14. A method of increasing the absorption of a nutrient in a subject in need of such an increase, comprising administering the nutrient and a nutrient absorption increasing effective amount of tetrahydropiperine, or an analog or derivative thereof, to said subject, wherein the nutrient is selected from the group consisting of amino acids, carbohydrates, vitamins, herbal extracts and antioxidants.

15. The method of claim 14, wherein the nutrient is selected from the group consisting of amino acids, carbohydrates, vitamins and herbal extracts.

16. The method of claim 14, wherein the nutrient and the tetrahydropiperine, or an analog or derivative thereof, are administered proximate in time to each other.

17. The method of claim 14, wherein said absorption is dermal or oral.

18. The method of claim 17, wherein said absorption is oral.

19. The method of claim 11, wherein the analog or derivative is
   alkyltetrahydropiperine, dialkyltetrahydropiperine, alkoxylated tetrahydropiperine, hydroxylated tetrahydropiperine, halogenated tetrahydropiperine, dihydropiperine, alkyldihydropiperine, dialkyldihydropiperine, alkoxylated dihydropiperine, hydroxylated dihydropiperine, or halogenated dihydropiperine, wherein alkyl is of 1 to 6 carbon atoms and dialkyl are two alkyl groups independently of 1 to 6 carbon atoms.

20. The method of claim 14, wherein the analog or derivative is
   alkyltetrahydropiperine, dialkyltetrahydropiperine, alkoxylated tetrahydropiperine, hydroxylated tetrahydropiperine, halogenated tetrahydropiperine, dihydropiperine, alkyldihydropiperine, dialkyldihydropiperine, alkoxylated dihydropiperine, hydroxylated dihydropiperine, or halogenated dihydropiperine, wherein alkyl is of 1 to 6 carbon atoms and dialkyl are two alkyl groups independent of 1 to 6 carbon atoms.

21. A method of increasing the absorption of a nutrient in a subject, comprising administering the nutrient and a nutrient absorption increasing effective amount of tetrahydropiperine, or an analog or derivative thereof, to said subject, wherein the nutrient is selected from the group consisting of amino acids, carbohydrates, vitamins, herbal extracts and antioxidants.

* * * * *